(12) United States Patent
Zhang et al.

(10) Patent No.: US 8,198,344 B2
(45) Date of Patent: Jun. 12, 2012

(54) METHOD OF PREPARING ADHESIVE COMPOSITIONS FOR MEDICAL USE: SINGLE ADDITIVE AS BOTH THE THICKENING AGENT AND THE ACCELERATOR

(75) Inventors: Sheng Zhang, Hudson, NC (US); Rafael Ruiz, Hudson, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 1022 days.

(21) Appl. No.: 12/214,794

(22) Filed: Jun. 20, 2008

(65) Prior Publication Data
US 2009/0317353 A1    Dec. 24, 2009

(51) Int. Cl.
*A62B 17/08*    (2006.01)
*C08J 3/28*    (2006.01)
*C09J 4/04*    (2006.01)
*C08K 5/13*    (2006.01)

(52) U.S. Cl. ......... 522/79; 424/78.02; 514/527; 522/71; 522/74; 522/75; 522/76; 522/173; 523/111

(58) Field of Classification Search ............... 424/78.02; 522/71, 74, 75, 76, 79, 173; 523/111; 514/527
See application file for complete search history.

(56) References Cited

U.S. PATENT DOCUMENTS

| | | |
|---|---|---|
| 211,104 A | 1/1879 | Mulford |
| 334,046 A | 1/1886 | Pinkham |
| 1,221,227 A | 4/1917 | Schulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |
| 3,742,018 A | 6/1973 | O'Sullivan |
| 3,779,706 A | 12/1973 | Nablo |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |
| 3,924,623 A | 12/1975 | Avery |
| 3,941,488 A | 3/1976 | Maxwell |
| 3,975,422 A | 8/1976 | Buck |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |
| 4,102,945 A | 7/1978 | Gleave |
| 4,105,715 A | 8/1978 | Gleave |
| 4,109,037 A | 8/1978 | Nohara |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,265,948 A | 5/1981 | Hayes et al. |
| 4,310,509 A | 1/1982 | Berglund et al. |
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |

(Continued)

FOREIGN PATENT DOCUMENTS
DE    2 261 261    7/1973
(Continued)

OTHER PUBLICATIONS

"Aclar®/Barex® Laminates: Flexible Solutions for Pharma Packaging" Drug Delivery Technology vol. 3, No. 3, May 2003, Posted on Mar. 28, 2008, http://www.drugdeliverytech.com/ME2/dirmod.asp?sid=&nm=&type=Publishing& mod=Publications %3A% 3AArticle&mid=8F3A7027421841978F18BE895F87F791&tier=4& id=6EC6964EB29D46D8A297E499E57A4164.

Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

Cameron, J.L. et al., "The Degradation of Cyanoacrylate Tissue Adhesive, pt. 1", Surgery, vol. 58, Iss. 2, Aug. 1965, pp. 424-430.

Collins et al., "Biological Substrates and Cure Rates of Cyanoacrylate Tissue Adhesives" Archives of Surgery vol. 93, Sep. 1966, 428-432.

Darwish et al., "The evaluation of crown ether based niosomes as cation containing and cation sensitive drug delivery systems" International Journal of Pharmaceutics 159 (1997) 207-213.

(Continued)

*Primary Examiner* — Ana Woodward
(74) *Attorney, Agent, or Firm* — Stradley Ronon Stevens & Young, LLP

(57) ABSTRACT

The present invention relates to compositions of cyanoacrylate monomer, a method of improving the viscosity and the curing speed with a single additive and a process of providing sterilized cyanoacrylate adhesive compositions for application in the medical field.

20 Claims, No Drawings

U.S. PATENT DOCUMENTS

| | | | |
|---|---|---|---|
| 4,377,490 A | 3/1983 | Shiraishi et al. |
| 4,386,193 A | 5/1983 | Reich et al. |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,713,235 A | 12/1987 | Krall |
| 4,718,966 A | 1/1988 | Harris et al. |
| 4,772,148 A | 9/1988 | Buschemeyer |
| 4,786,534 A | 11/1988 | Aiken |
| 4,818,325 A | 4/1989 | Hiraiwa et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,994,542 A | 2/1991 | Matsuda et al. |
| 5,009,654 A | 4/1991 | Minshall et al. |
| 5,039,753 A | 8/1991 | Woods et al. |
| 5,042,690 A | 8/1991 | O'Meara |
| 5,051,256 A | 9/1991 | Barnes |
| 5,069,907 A | 12/1991 | Mixon et al. |
| 5,083,685 A | 1/1992 | Amemiya et al. |
| 5,131,777 A | 7/1992 | Kimura et al. |
| 5,135,964 A | 8/1992 | Lee et al. |
| 5,167,616 A | 12/1992 | Haak et al. |
| 5,169,383 A | 12/1992 | Gyory et al. |
| 5,192,536 A | 3/1993 | Huprich |
| 5,225,182 A | 7/1993 | Sharma |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,530,037 A | 6/1996 | McDonnell et al. |
| 5,547,662 A | 8/1996 | Khan et al. |
| 5,561,198 A | 10/1996 | Huver et al. |
| 5,665,817 A | 9/1997 | Greff et al. |
| 5,684,042 A | 11/1997 | Greff et al. |
| 5,730,994 A | 3/1998 | Askill et al. |
| 5,749,956 A | 5/1998 | Fisher et al. |
| 5,803,086 A | 9/1998 | Scholz et al. |
| 5,807,563 A | 9/1998 | Askill et al. |
| 5,874,044 A | 2/1999 | Kotzev |
| 5,902,594 A | 5/1999 | Greff et al. |
| 5,916,882 A | 6/1999 | Jeng |
| 5,928,611 A | 7/1999 | Leung |
| 5,944,754 A | 8/1999 | Vacanti |
| 5,957,877 A | 9/1999 | Askill et al. |
| 5,979,450 A | 11/1999 | Baker et al. |
| 5,981,621 A | 11/1999 | Clark et al. |
| 5,985,395 A | 11/1999 | Comstock et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,323,275 B2 | 11/2001 | Takahashi et al. |
| 6,352,704 B1 | 3/2002 | Nicholson et al. |
| 6,488,665 B1 | 12/2002 | Severin et al. |
| 6,492,434 B1 | 12/2002 | Barley, Jr. et al. |
| 6,495,229 B1 | 12/2002 | Carte et al. |
| 6,547,917 B1 | 4/2003 | Misiak et al. |
| 6,579,469 B1 | 6/2003 | Nicholson et al. |
| 6,620,846 B1 | 9/2003 | Jonn et al. |
| 6,626,296 B1 | 9/2003 | Jimu et al. |
| 6,667,031 B2 | 12/2003 | Azevedo |
| 6,699,940 B2 | 3/2004 | Shalaby |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B1 | 9/2004 | Kotzev |
| 6,802,416 B1 | 10/2004 | D'Alessio et al. |
| 6,849,082 B2 | 2/2005 | Azevedo |
| 6,881,421 B1 | 4/2005 | da Silveira et al. |
| 6,896,838 B2 | 5/2005 | D'Alessio |
| 6,942,875 B2 | 9/2005 | Hedgpeth |
| 6,960,040 B2 | 11/2005 | D'Alessio et al. |
| 6,974,585 B2 | 12/2005 | Askill |
| 6,977,278 B1 | 12/2005 | Misiak |
| 6,995,227 B2 | 2/2006 | Ryan et al. |
| 7,255,874 B1 | 8/2007 | Bobo et al. |
| 2002/0002223 A1 | 1/2002 | Cox et al. |
| 2002/0037272 A1 | 3/2002 | Askill et al. |
| 2003/0044380 A1 | 3/2003 | Zhu et al. |
| 2003/0077386 A1 | 4/2003 | Azevedo |
| 2003/0135016 A1 | 7/2003 | Tajima et al. |
| 2003/0158579 A1 | 8/2003 | Azevedo |
| 2003/0158580 A1 | 8/2003 | Azevedo |
| 2004/0115274 A1 | 6/2004 | Cox et al. |
| 2004/0126355 A1 | 7/2004 | Childers |
| 2004/0127738 A1 | 7/2004 | Azevedo |
| 2004/0253039 A1 | 12/2004 | Stenton |
| 2005/0047846 A1 | 3/2005 | Narang et al. |
| 2005/0067312 A1 | 3/2005 | Gupta et al. |
| 2005/0142163 A1 | 6/2005 | Hunter et al. |
| 2005/0147582 A1 | 7/2005 | Zimmerman et al. |
| 2005/0182347 A1 | 8/2005 | Bishop et al. |
| 2005/0196431 A1 | 9/2005 | Narang et al. |
| 2005/0197421 A1 | 9/2005 | Loomis |
| 2005/0281866 A1 | 12/2005 | Jarrett et al. |
| 2005/0284487 A1 | 12/2005 | Gellerstedt et al. |
| 2006/0062687 A1 | 3/2006 | Morales |
| 2007/0041935 A1 | 2/2007 | Salamone et al. |
| 2007/0048356 A1 | 3/2007 | Schorr et al. |
| 2007/0078207 A1 | 4/2007 | Jonn et al. |
| 2007/0092481 A1 | 4/2007 | Misiak et al. |
| 2007/0092483 A1 | 4/2007 | Pollock |
| 2007/0147947 A1 | 6/2007 | Stenton et al. |
| 2008/0021139 A1 | 1/2008 | Blacklock et al. |
| 2008/0078413 A1 | 4/2008 | Padget et al. |
| 2008/0102053 A1 | 5/2008 | Childers |
| 2008/0319063 A1 | 12/2008 | Zhang |
| 2010/0035997 A1 | 2/2010 | Broadley et al. |
| 2010/0269749 A1* | 10/2010 | Badejo et al. ............... 118/300 |

FOREIGN PATENT DOCUMENTS

| | | |
|---|---|---|
| DE | 40 09 621 | 10/1991 |
| DE | 2010 3336 | 5/2001 |
| DE | 10 2007 019 044 | 10/2008 |
| EP | 0127466 | 12/1984 |
| EP | 0271675 | 6/1988 |
| FR | 2700698 | 7/1994 |
| GB | 1 230 560 | 5/1971 |
| GB | 2200124 | 7/1988 |
| JP | 59-066471 | 4/1984 |
| JP | 62-022877 | 1/1987 |
| JP | 03-207778 | 9/1991 |
| JP | 10-140091 | 5/1998 |
| WO | WO96/14292 | 5/1996 |
| WO | WO96/23532 | 8/1996 |
| WO | WO99/10020 | 3/1999 |
| WO | WO03/070257 | 8/2003 |
| WO | WO2004/045498 | 6/2004 |
| WO | WO2006/073922 | 7/2006 |
| WO | WO2009/003017 | 12/2008 |
| WO | WO2009/064291 | 5/2009 |

OTHER PUBLICATIONS

Dumont et al., "New Oligosaccharidic Crown Ethers as Potential Drug-Targetting Vectors: Synthesis & Biological Evaluation" Bioorganic & Medicinal Chemistry Letters, vol. 4, No. 9, pp. 1123-1126, 1994.

Fussnegger, B. "Poloxamers (1) Lutrol® F 68 (Poloxamer 188)." BASF ExAct, No. 3, Nov. 1999, 5-6.

Garnier-Suillerot et al., "Analysis of Drug Transport Kinetics in Multidrug-resistant Cells: Implications for Drug Action" Current Medicinal Chemistry, 2001, 8, 51-64.

Hansen, "Fast Cure—High moisture vapor transmission rate adhesives improve wound care." Adhesives Age Mar. 2003, pp. 22, 24 and 25.

International Search Report and Written Opinion dated Jul. 28, 2010 for international application No. PCT/US2009/048130.

Lehman et al., "Toxicity of Alkyl 2-Cyanoacrylates", Archives of Surgery, vol. 93, Issue 3, Sep. 1966, pp. 441-446.

Leonard, F., "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Alkyl a-Cyanoacrylate Homologs", Journal of Applied Polymer Science, vol. 10 1966, pp. 1617-1623.

Leonard, F. et al., "Synthesis and Degradation of Poly (alkyl a-Cyanoacrylates)", Journal of Applied Polymer Science, vol. 10, Iss 8, Aug. 1966, p. 1214.

Leonard, F. et al., "Synthesis and Degradation of Poly(alkyl a-Cyanoacrylates)", Journal of Applied Polymer Science, vol. 10, Iss. 2, Feb. 1966, pp. 259-272.

Material Safety Data Sheet (MSDS) of 2-octyl cyanoacrylate; Jun. 2, 2004.

Material Safety Data Sheet (MSDS) of isobuthyl-2-cyanoacrylate; Sep. 25, 1998.

Material Safety Data Sheet (MSDS) of n-butyl cyanoacrylate; Oct. 19, 2009 and Jun. 2, 2004.

Tseng, Y.C. et al., "Modification of synthesis and investigation of properties for 2-cyanoacrylates", Biomaterials, vol. 11, Jan. 1990, pp. 73-79.

Uchegbu et al., "Non-ionic surfactant based vesicles (niosomes) in drug delivery" International Journal of Pharmaceutics 172 (1998) 33-70.

Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.

Vezin, W.R. et al., "In vitro heterogeneous degradation of poly(n-alkyl a-cyanoacrylates)", Journal of Biomedical Materials Research, vol. 14, 1980, pp. 93-106.

Woodward, S.C. et al., "Histotoxicity of Cyanoacrylate Tissue Adhesives in the Rat", Annals of Surgery, vol. 162, No. 1, Jul. 1965, pp. 113-122.

Yonezawa, M. et al., "Studies on a-Cyanoacrylate, VI: Reaction of Cyanoacetate with Formaldehyde" Yuki Gosei Kagaku Kyokaishi, vol. 25, Iss 4, Apr. 1967, pp. 311-316.

\* cited by examiner

METHOD OF PREPARING ADHESIVE COMPOSITIONS FOR MEDICAL USE: SINGLE ADDITIVE AS BOTH THE THICKENING AGENT AND THE ACCELERATOR

BACKGROUND OF THE INVENTION

1. Field of the Invention

The present invention relates to compositions of cyanoacrylate monomer, a method of improving the viscosity and the curing speed with a single additive and a process of providing sterilized cyanoacrylate adhesive compositions for application in the medical field.

2. Description of Related Art

Adhesive compositions based upon cyanoacrylate ester are known and have been used extensively in different fields due to their excellent long-term bond strength and applicability to a large range of substrates. These adhesive compositions are used as industrial and structural adhesives, consumer product for repair of household items and in the hobby sector for assembly and repair. In addition, cyanoacrylate compositions have found application in medicine for closing wounds especially in cases where suturing does not provide satisfactory results. Cyanoacrylate esters are used in protecting surface injuries including abrasions, lacerations, sores, burns and other open surface wounds.

In spite of their interesting properties and wide applications in different fields, certain factors have been an impediment to further application of cyanoacrylate adhesive compositions. One of the problems encountered results from the low inherent viscosity of cyanoacrylate monomers. Another related issue is the slow cure speed provided by certain cyanoacrylate compositions after stabilization of the compositions with various polymerization inhibitors. In addition, some cyanoacrylate adhesive compositions do not provide long-term stability especially after the sterilization. Cyanoacrylate adhesives combined with certain additives may cause significant histological response.

Cyanoacrylate adhesives are usually in the monomeric form when applied to a substrate. The subsequent polymerization of the cyanoacrylate affords the desired adhesive bond. However, the monomeric form of cyanoacrylate has a very low inherent viscosity which can result in the spreading of the adhesive into undesired areas. In order to obtain a cyanoacrylate adhesive composition with a desired higher viscosity, different thickening agents have been added to the adhesive compositions.

Organic or inorganic powders, which are not soluble in cyanoacrylate monomer, have been used as fillers to adjust the viscosity of cyanoacrylate compositions. Such materials include various inert inorganic materials such as silica, quartz, alumina, calcium and metal salts and organic powders such as polycarbonates, polyvinylidene fluorides, polyethylenes, and other polymeric powders. U.S. Pat. No. 4,533,422 discloses that cyanoacrylate compositions which employ fumed silicas as the filler are stable and exhibit a high thixotropic ratio. U.S. Pat. No. 3,607,542 discloses the preparation of a water-resistant cyanoacrylate paste containing insoluble, inert fillers such as salts of calcium, titanium, zinc, tin, aluminum, iron and copper, among others. U.S. Pat. No. 4,105,715 discloses the use of finely divided organic powders such as polycarbonates, polyvinylidene fluorides, polyethylenes, and other polymeric powders as additives for cyanoacrylates. Blending insolvable materials with cyanoacrylate compositions can cause separation while the adhesive is stored, resulting in ineffective modification of the viscosity. Also, the presence of the fillers can sometimes affect the quality of the adhesive bonding.

The most effective attempt so far to improve the viscosity of the cyanoacrylate adhesive compositions is combining various polymer additives to the cyanoacrylate monomer compositions. The polymer additives are soluble in cyanoacrylate compositions either at room or at elevated temperature.

For example, U.S. Pat. No. 3,282,773 to Wicker discloses cyanoacrylate adhesive compositions in which poly (methylmethacrylate) is used as the thickener.

U.S. Pat. No. 3,527,841 to Wicker et al. discloses a 2-cyanoacrylate adhesive composition for general use as well as for surgical use containing poly (lactic acid) as the viscosity thickener and an acidic compound such as sulfur dioxide and a free radical stabilizer such as hydroquinone.

U.S. Pat. No. 3,692,752 to Setsuda et al. discloses thickened cyanoacrylate solutions containing certain polyether acrylates/methacrylates, acrylic/methacrylic esters of bis(hydroxyalkyl) phosphonic acid derivatives, and acrylic/methacrylic esters of tris(hydroxyalkyl) cyanuric acid derivatives.

U.S. Pat. No. 4,102,945 to Gleave discloses a cyanoacrylate adhesive composition thickened by a copolymer or terpolymer resin capable of being dissolved or solvated by the cyanoacrylate monomer. Such cyanoacrylate adhesives exhibit significantly improved peel strength. Polymer thickeners disclosed by Gleave are acrylonitrile-butadiene-styrene terpolymers, methacrylate-butadiene-styrene terpolymers, and vinylidene chloride-acrylonitrile copolymers.

U.S. Pat. No. 5,328,687 to Leung et al. also discloses adhesive compositions that may be used for bonding tissue. The compositions contain polymers as thickening agents. Polymer thickeners employed include polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

U.S. Pat. No. 5,350,789 to Linden et al. discloses 2-cyanoacrylate-based tissue adhesives employing biocompatible oxalate polymers as reactive plasticizers and thickening agents. The adhesives are capable of being formulated to allow modulus matching of the adhesive and the substrate.

U.S. Pat. No. 5,665,817 to Greff et al. discloses alkyl cyanoacrylate compositions suitable for topical application to human skin, which comprise a suitable amount of a thickening agent to increase the viscosity. The thickening agent used is any biocompatible material that increases the viscosity of an alkyl cyanoacrylate composition including polymethylmethacrylate (PMMA) or other preformed polymers soluble in the alkyl cyanoacrylate. The thickening agent is added to provide a viscosity of from about 2 to 50,000 centipoises at 20° C.

U.S. Pat. No. 6,299,631 to Shalaby discloses bio-absorbable adhesive/hemostatic formulations of a 2-alkoxyalkylcyanoacrylate with trimethylene carbonate-based polymers as the viscosity thickener.

U.S. Pat. No. 4,038,345 to O'Sullivan et al. discloses stable cyanoacrylate adhesive compositions having improved viscosities. The adhesive compositions have viscosities in excess of about 500 centipoises comprising at least one monomeric ester of 2-cyanoacrylic acid, and a polyacrylate thickener which was pretreated to have a reduced viscosity greater than about 5. A free radical polymerization initiator in the amount of less than about one percent by weight is disclosed. The composition also contains an inhibitor for the anionic polymerization of the monomer. O'Sullivan discloses a process for preparing improved cyanoacrylates which involves heating a conventional polyacrylate thickener at a suitable temperature and for a suitable period of time to reduce its content of free radical polymerization initiators to below about one percent; and dissolving a sufficient amount of polymer thickener in the ester of 2-cyanoacrylic acid to produce a cyanoacrylate adhesive composition with suitable viscosity.

U.S. Pat. No. 6,797,107 to Kotzey et al. discloses a solid cyanoacrylate adhesive composition which can be applied to a substrate in solid form and which polymerizes into an adhesive polymer upon liquefying. The solid cyanoacrylate composition liquefies at temperatures slightly above room temperature and polymerizes upon liquification. $\epsilon$-caprolactones are used as a solidifying polymer with cyanoacrylate monomers and other additives to form the solid cyanoacrylate adhesive composition.

U.S. Pat. No. 6,743,858 to Hickey et al. discloses a method of making a thickened sterile monomeric adhesive composition. Preparation of the composition includes placing a mixture of a polymerizable monomer and a thickening agent in a container, sealing the container and sterilizing the container and the mixture. The thickening agent is soluble in the monomer at room temperature. Suitable thickeners employed include, for example, polyoxalates, lactic-glycolic acid copolymers, polycaprolactone, lactic acid-caprolactone copolymers, poly (caporolactone+DL-lactide+glycolide), polyorthoesters, polyalkyl acrylates, copolymers of alkylacrylate and vinyl acetate, polyalkyl methacrylates, and copolymers of alkyl methacrylates and butadiene.

U.S. Pat. Appl. No. 20070092481 to Misiak et al. discloses a thickened cyanoacrylate adhesive composition by using poly[butyleneterephthalate-co-poly(ethyleneglycol) terephthalate] as the viscosity modifier. The formulation of cyanoacrylate adhesives in the form of low viscosity emulsions, non-flowable and gels forms could be prepared by adding this polymer component to the compositions.

Polymers of cyanoacrylates has also been used to modify the cyanoacrylate adhesive compositions. U.S. Pat. No 2,794,788 teaches thickening of cyanoacrylate adhesives by dissolving polymeric alkyl cyanoacrylates, as well as other compounds including methacrylates, polyacrylates and cellulose esters. U.S. Pat. No. 3,527,224 to Rabinowitz discloses a surgical adhesive composition comprising monomeric and polymeric n-pentyl cyanoacrylate obtained by free-radical polymerization. U.S. Pat. Appl. No. 20060062687 to Morales discloses a method of sterilizing 2-cyanoacrylate compositions with poly-cyanoacrylate as the thickener, including heating the composition in a device at a temperature of from about 70° C. to about 140° C. for an effective amount of time. Morales discloses sterilization assays and 2-cyanoacrylate compositions for use in medicine or surgery. U.S. Pat. No. 3,564,078 discloses the use of poly (ethyl 2-cyanoacrylate) as a component of cyanoacrylate compositions.

The polymer additives previously used to improve the viscosity of the cyanoacrylate adhesive have not satisfactorily solved the conventional problem of this type of adhesive which is providing a stable, higher viscosity cyanoacrylate adhesive with properties desirable for medical applications. In some cases, only a relatively small modification of the viscosity is achieved by addition of polymers because the amount of the polymer thickener that can be added is limited due to the poor solubility of these polymers in the cyanoacrylate monomer. Adding too much polymer thickener to the adhesive compositions will result in spinnability, reduction of optical clarity and weakening of the adhesive bond. In addition, many polymer additives used as the thickening agents undergo decomposition under sterilization, which leads to the decreased viscosity. The instability of these cyanoacrylate adhesive compositions is exacerbated by the use of acid stabilizers. Acids destabilize the polymer thickener in these compositions. Presently, the only polymer thickeners which can be successfully used for commercial cyanoacrylate adhesive compositions include poly (methylmethacrylate) or poly (vinylacetate).

Another problem associated with cyanoacrylate adhesives is the relatively slow cure speed, especially those in compositions stabilized with a large amount of free radical and acid stabilizers. Cyanoacrylate adhesive compositions readily polymerize and cure in a short time without any catalysts or heating in the presence of anionic activators such as moisture or alkaline substances present on the solid substrates. However, the cure speed of the adhesives can be dramatically decreased if cyanoacrylate adhesives are applied to acidic substrates such as wood and paper. In addition, if a large amount of adhesive is applied in a relatively thick layer for example in a joint gap, rapid hardening throughout the adhesive may be difficult to achieve. In these cases, cyanoacrylate adhesives with a faster cure speed would provide a solution to these problems.

Various attempts have been made to shorten the cure time of cyanoacrylate adhesives. Different chemicals have been added to the cyanoacrylate adhesive compositions for this purpose. Accelerators used previously include detergent compositions; surfactants, amines, heterocyclic compounds, caffeine, aniline derivatives, urea, phosphines, alcohols, aromatic and aliphatic polyols, polyethylene glycols, inorganic bases and salts, sulfur compounds, polymeric cyclic ethers, crown ethers, calixarenes, cyclic and acyclic carbonates, and organometallics.

Japanese Patent Application No. JP-A-03 207 778 discloses the use of solutions of aliphatic, alicyclic and, especially, tertiary aromatic amines as the activators for the curing of cyanoacrylate adhesives. Specific examples included N,N-dimethylbenzylamine, N-methylmorpholine and N,N-diethyltoluidine. Japanese Patent Application No. JP-A-62 022 877 suggested the use of solutions of lower fatty amines, aromatic amines, and dimethylamine for the same purpose.

U.S. Pat. No. 4,042,442 to Dombroski et al. discloses the addition of a polymerization initiator such as caffeine or theobromine to a cyanoacrylate adhesive composition. The caffeine or theobromine may be added to the adhesive composition in different ways. The caffeine or theobromine can be dissolved in a volatile solvent, the volatile solvent is allowed to evaporate, and then the cyanoacrylate adhesive composition is applied to the surfaces of the substrates to be joined. Alternatively, the caffeine or theobromine can be mixed with the cyanoacrylate adhesive composition by stirring just prior to application of the adhesive to the substrates to be joined. Both of these methods are inconvenient for the user because two separate solutions or two separate applications are required.

British Patent No. 1 230 560 described cyanoacrylate adhesive compositions containing certain substituted heterocyclic compounds as accelerators. The compositions may be presented in a two-part form, the first part comprising the cyanoacrylate adhesive and the second part comprising at least one of the substituted heterocyclic compounds, preferably dissolved in an organic solvent. The heterocyclic compound is invariably present in one part of a two-part composition because iminoethylene-substituted triazines and pyrimido-ypyrimidines accelerate the polymerization so rapidly that they must be kept from the cyanoacryalte composition before use. An effective adhesive bond is obtained. This reference does not disclose an activator which is able to initiate polymerization throughout a layer of adhesive.

In U.S. Pat. No. 4,170,585 to Motegi et al., certain polyethylene glycols and poly (ethyleneoxy) are disclosed as additives for improving the curing speed of the cyanoacrylate compositions. In U.S. Pat. No. 4,377,490, aliphatic polyether and polyols have been used to modify 2-cyanoacrylate adhesive compositions.

U.S. Pat. No. 4,718,966 to Stephen. et al. discloses that cyanoacrylate adhesive compositions with calixarene compounds as accelerators give substantially reduced cure times on substrates such as wood, leather, ceramic, plastics and metals. The calixarene compounds are preferably employed at levels of about 0.1-1% by weight of the composition.

Japanese Patent Application No. 8-310136 to Ohashi, et al. discloses 2-cyanoacrylate adhesive compositions containing a crown ether or a polyalkylene oxide as the curing accelerator.

DE-A-40 09 621 proposed the use of certain cyclodextrin derivatives as additives to improve the cure speed of cyanoacrylate adhesives, some of which are soluble in cyanoacrylates. GB-A-2 200 124 revealed the use of acyclic phenol-formaldehyde oligomers as the accelerating additive for cyanoacrylate adhesive compositions.

Besides mixing the accelerators with the 2-cyanoacrylate adhesive, two component systems have also been proposed that package the cyanoacrylate adhesive and the accelerator separately. The disadvantage of this method is that accurate measurement of the accelerator and appropriate homogeneous mixing of the two components is difficult to achieve since only a trace amount of accelerator is generally required. U.S. Pat. No. 5,928,611 to Leung disclosed an applicator tip for dispensing a polymerizable material, in which a polymerization accelerator was included. The accelerator initiates polymerization when the cyanoacrylate adhesive liquid is dispensed through the applicator tip. Suitable accelerators include detergent compositions; surfactants, amines, urea, phosphines, alcohols, inorganic bases and salts, sulfur compounds, polymeric cyclic ethers, crown ethers, calixarenes, cyclic and acyclic carbonates, organometallics, and radical.

As illustrated above, a wide range of chemicals (small molecules or polymers) have been incorporated into the cyanoacrylate adhesive compositions either to improve the curing speed or to increase the viscosity of cyanoacrylate adhesives. However, most of the employed additives (thickeners or accelerators) exhibit various disadvantagest. Some of the accelerators or thickeners are toxic, while others exhibit weak effect, less bond strength, high volatility and odor. In addition, irregular structure is formed in some cases, which destroys transparency of the cyanoacrylate polymer film. Moreover, the stability and shelf life of cyanoacrylate adhesive compositions containing thickening agents or polymerization accelerators are always less than desirable. These shortcomings limit the application of the cyanoacrylate adhesives in different fields, especially for medical use. One goal of the present invention is, therefore, to use pluronic polymer additives to improve both the curing speed and the viscosity of the cyanoacrylate adhesives, particularly for use in medical applications.

SUMMARY OF THE INVENTION

The current invention provides a sterilized cyanoacrylate adhesive composition with one or more pluronic polymer(s) as additive(s) to act as both polymerization accelerator and thickening agent. Preferably a single pluronic polymer is added to the cyanoacrylate to serve as both polymerization and thickening agent. Cyanoacrylate adhesive compositions with various viscosities having cure speeds of about 5 seconds to about 60 seconds, preferably form about 10 to about 50 seconds and more preferably from about 15 to about 35 seconds can be prepared by the methods of the present invention.

The current invention provides cyanoacrylate compositions with a small amount of polymer additive(s). Usually, only from about 0.04% to about 0.50% of pluronic polymer by weight of the cyanoacryalate adhesive composition is introduced to the adhesive composition and more preferably only from about 0.06% to about 0.20 % of polymer additive by weight of cyanoacrylate compositions is incorporated.

The current invention provides a method of preparing cyanoacrylate adhesive compositions with a fast cure speed by heating the cyanoacrylate monomer in the presence of a small amount of pluronic additive at from about 40 to about 60° C. for about 1 to 2.5 hours The current invention provides a method of controlling the viscosity level of cyanoacrylate adhesive compositions. Cyanoacrylate adhesive compositions with any desired level of viscosity may be readily prepared by modifying the amount of pluronic polymer and the stabilizers present in the cyanoacrylate monomer.

The current invention provides methods of preparing the sterilized cyanoacrylate adhesive composition by sterilizing the composition after introducing the pluronic polymer additive. The pluronic polymer additive may be biocompatible, which makes the cyanoacrylate compositions especially suitable for medical use.

The current invention also provides for methods of sealing tissue by spreading the sterilized cyanoacrylate adhesive composition with a desired viscosity onto the tissue, which is quickly cured to seal the tissue. Other advantages of the current invention will become obvious as disclosed in the detailed descriptions.

DETAILED DESCRIPTION OF THE INVENTION

The present invention provides the sterilized cyanoacrylate adhesive compositions and a method of preparing cyanoacrylate compositions with a desired viscosity and a fast cure speed by incorporating a single type of polymer additive into the cyanoacrylate adhesive.

The sterilized cyanoacrylate adhesive composition can be used as tissue adhesive for sealing and aiding in the repair of tissue.

The present invention provides sterilized cyanoacrylate adhesive compositions desired predetermined viscosity and fast curing speed while reducing undesired side reactions. It is well known that cyanoacrylate monomer is very sensitive to premature polymerization. Once polymerization is initiated, curing of the adhesive can occur very rapidly, making it very difficult to control the polymerization rate. This propensity for premature polymerization creates the challenge of thickening of the cyanoacrylate adhesive compositions via partial polymerizing of the cyanoacrylate monomer. The present invention provides a method to overcome such challenge by heating the cyanoacrylate monomer at about 40 to about 60° C. in the presence of pluronic polymer.

Pluronics, the tradename for poloxamers, are nonionic triblock copolymers composed of a central hydrophobic chain of polyoxypropylene flanked by two hydrophilic chains of polyoxyethylene. Because the lengths of the polymer blocks can be customized, many different poloxamers exhibit slightly different properties. For the generic term poloxamer these copolymers are commonly named with the letter "P" followed by three digits, the first two digits times 100 gives the approximate molecular mass of the polyoxypropylene core and the last digit times 10 gives the percentage polyethylene content (e.g. P407=poloxamer with a polyoxypropylene molecular mass of 4000 g/mole and a 70% polyoxyethylene content). For the Pluronic tradename, coding of these copolymers starts with a letter to define its physical form (L=liquid, P=paste, F=flake (solid)) followed by two or three digits. The first digit(s) refer to the molecular mass of the polyoxypropylene core (determined from BASF's Pluronic grid) and the last digit times 10 gives the percentage polyoxyethylene content (e.g. Pluronic F127 =pluronic with a polyoxypropylene molecular mass of 4000 g/mol and a 70% polyoxyethylene content. Therefore P407 defines the same poloxamer as Pluroninc F127. The general structure of pluronic polymer is shown below. The pluronic polymers used in the present invention are difunctional block copolymer surfactants that terminate in primary hydroxyl groups. The very small percentage of hydroxyl groups in the molecule makes the pluronic polymer a mild polymerization initiator for cyanoacrylate monomer. The polymerization rate can be readily controlled by modifying the amount of pluronic polymer and polymerization inhibitor present in the cyanoacrylate adhesive compositions.

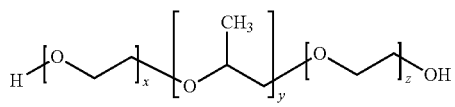

a-Hydro-w-hydroxypoly(oxyethylene)$_x$poly(oxypropylene)$_y$poly(oxyethylene)$_z$ block polymer The chart below demonstrates some of the possible values of x, y and z for poloxamers.

| Poloxamer | x | y | z |
|---|---|---|---|
| 124 | 12 | 20 | 12 |
| 188 | 80 | 27 | 80 |
| 237 | 64 | 37 | 64 |
| 338 | 141 | 44 | 141 |
| 407 | 101 | 56 | 101 |

The pluronic polymers used in this invention include preferably pluronic F38 prill, pluronic F68 prill, pluronic F88, pluronic F108NF and pluronic F127 prill, in the preferable amount 0.02 to 0.5%. Any other suitable pluronic polymer additive, such as, but not limited to, pluronic 10R5, pluronic 17R2, pluronic 17R4, pluronic 25R2, pluronic 25R4, pluronic 31R1, pluronic F68 LF, pluronic F68NF, pluronic F68NF prill poloxamer 188, pluronic F77, pluronic F87, pluronic F98, pluronic F108, pluronic F127, pluronic F127 NF, pluronic F127 NF prill poloxamer407, pluronic L 10, pluronic L 101, pluronic, L121, pluronic L 31, pluronic L 35, pluronic, L 43, pluronic L44, pluronic, L44 NF poloxamer 124, pluronic, L 61, pluronic 62, pluronic L62 LF, pluronic, L 62D, pluronic L64, pluronic L 81, pluronic L 92, pluronic N 3, pluronic P 103, pluronic P 104, pluronic P 105, pluronic P 123 surfactant, pluronic P 65, pluronic, P 84 and pluronic P 85, can also be used (Pluronic polymers were obtained from BASF Corporation, 100 Campus Drive, Florham Park, N.J., USA).

Using biocompatible pluronic polymers as the additive makes the said cyanoacrylate adhesive compositions of the current invention especially suitable for medical use. Pluronic polymer such as pluronic F127 has been approved by FDA for medical use and they are biocompatible and therefore are especially suitable for use in cyanoacrylate adhesives as medical adhesives.

Both the viscosity and the cure speed of cyanoacrylate adhesive composition are dependent upon the amount of the pluronic polymer additive applied. The compositions produced, packaged and sterilized according to the current invention provide adhesive compositions with a wide range of viscosities with a faster cure speed compared to cyanoacrylate adhesive compositions of the prior art.

As described herein, the present invention provides a method of preparing cyanoacrylate ester compositions by combining polymer additive and cyanoacrylate at elevated temperatures. Pluronic polymers are not soluble in cyanoacrylate adhesive compositions at room temperature. However, pluronic polymers may be dissolved in cyanoacrylate monomer at elevated temperatures. The present invention provides a method to overcome such challenge by heating the cyanoacrylate monomer at the temperature range of about 30 to about 70° C., preferably from about 40 to about 65° C., and more preferably from about 50 to about 60° C. in the presence of pluronic polymer. After its dissolution in cyanoacrylate adhesive, pluronic polymer induces the partial polymerization of cyanoacrylate monomer to increase the viscosity to a desired level where upon the partial polymerization is immediately quenched by adding stabilizers.

In one embodiment of the present invention, cyanoacrylate adhesive compositions having a predetermined viscosity are prepared by adding pluronic polymer as the initiator at about 40 to about 60° C. to cyanoacrylate monomers pre-stabilized with different amounts of free radical and anionic polymerization inhibitors. According to the present invention, cyanoacrylate compositions of various viscosities including gels and non-flowable forms may be obtained. The viscosity level of the cyanoacrylate compositions of this invention may be controlled because pluronic polymers are mild polymerization initiators and partial polymerization of cyanoacrylate adhesive can be controlled by modifying the amount of pluronic polymer and polymerization inhibitor in the cyanoacrylate monomer. In a preferred embodiment of the present invention cyanoacrylate monomer, pre-stabilized with a certain amount of radical and anionic polymerization inhibitors is partially polymerized to provide the adhesive composition of this invention.

It is desirable to improve both the curing speed and increase the viscosity of the cyanoacrylate adhesives at the same time using a single polymer additive. Table 1 demonstrates that cyanoacrylate adhesive compositions with different viscosities can be obtained by applying suitable amount of pluronic polymer additives under various conditions. Monomeric cyanoacrylates subjected to partial polymerization in the presence of pluronic polymer with both radical and anionic polymerization inhibitors added provide cyanoacrylate compositions with a desired viscosity and a desired cure speed. As shown in Table 1, the cure time changes from about 70-90 s for the initial cyanoacrylate monomer with stabilizers to 12-19 s for the cyanoacrylate compositions with a desired level of high viscosity prepared by partial polymerization initiated by pluronic polymer. In the prior art methods an accelerator is incorporated to decrease the cure time and a polymer additives is used as the thickener to increase the viscosity of the cyanoacrylate adhesive compositions. In the present invention, pluronic polymer(s) can be used as an additive to increase the viscosity and reduce the cure speed of the cyanoacrylate compositions.

TABLE 1

Viscosity and set time results of the cyanoacrylate adhesive compositions with different level of viscosity.

| Entry | Percentage of Pluronic polymer | Average Viscosity (cps) | Average Set time (s) | Set time (s) of cyanoacrylate monomer[a] |
|---|---|---|---|---|
| 1 | 0.20% F127 | 362.7 | 16 | 77 s |
| 2 | 0.16% F38 | 51.9 | 15 | 75 s |
| 4 | 0.4% F68 | 182.5 | 12 | 72 s |
| 5 | 0.45% F88 | 107.7 | 19 | 81 s |
| 6 | 0.16% F127 | 58.9 | 17 | 86 s |

[a]Set time of the cyanoacrylate monomer pre-stabilized with polymerization inhibitor and before the addition of pluronic monomer.

Cyanoacrylate adhesive compositions of this invention may be prepared by cyanoacrylate monomer stabilized with different amount of radical and anionic polymerization inhibitors prior to the addition of the pluronic polymer. Table 2 shows examples of cyanoacrylate adhesive compositions of desired viscosity and cure speed prepared under various conditions. By modifying the conditions, cyanoacrylate adhesive compositions with any desired viscosity and set time may be prepared.

TABLE 2

Preparation of cyanoacrylate adhesive compositions under different conditions.

| | Amount of | Stabilizer[a] | | | | Performance of viscous adhesive | |
|---|---|---|---|---|---|---|---|
| Entry | polymer | BHA | SO$_2$ | Temp. | Mixing time | Viscosity (cp) | Set time (s) |
| 1 | 0.35% F68 | Yes | Yes | 40° C. | 3 hours | 13.3 | 13 |
| 2 | 0.3% F68 | Yes | Yes | 52° C. | 1.5 hours | 50.9 | 22 |
| 3 | 0.2% F68 | Yes | Yes | 60° C. | 1 hour | Gel[b] | 20 |
| 4 | 0.15% F68 | Yes | Yes | 60° C. | 2 hours | 115 | 25 |
| 5 | 0.16% F68 | Yes | Yes | 60° C. | 1.5 hours | 47.2 | 31 |
| 6 | 0.10% F68 | Yes | Yes | 60° C. | 3 hours | 420.9 | 31 |
| 7 | 0.10% F68 | Yes | Yes | 60° C. | 1.5 hours | 174.9 | 19 |
| 8 | 0.08% F68 | No | No | 52° C. | 1 hour | 52.3 | 19 |
| 9 | 0.07% F68 | No | No | 60° C. | 1 hour | 155.3 | 13 |
| 10 | 0.06% F68 | Yes | Yes | 45° C. | 2 hours | 7.36 | 15 |
| 11 | 0.20% F127 | Yes | Yes | 60° C. | 2 hours | 362.7 | 14 |
| 12 | 0.17% F127 | Yes | Yes | 60° C. | 2 hours | 281.6 | 19 |
| 13 | 0.15% F127 | Yes | Yes | 60° C. | 2 hours | Gel[b] | 25 |
| 14 | 0.12% F127 | Yes | Yes | 60° C. | 2.5 hours | 142.4 | 35 |
| 15 | 0.04% F127 | No | No | 60° C. | 1 hour | 50.5 | 35 |
| 16 | 0.45% F88 | Yes | Yes | 60° C. | 2 hours | 107.7 | 19 |
| 17 | 0.16% F88 | No | Yes | 60° C. | 2 hours | 118.5 | 19 |
| 18 | 0.20% F38 | Yes | Yes | 60° C. | 1.5 hours | Gel[b] | 16 |
| 19 | 0.16% F38 | Yes | Yes | 60° C. | 1.5 hours | 51.9 | 15 |
| 20 | 0.12% F38 | No | Yes | 60° C. | 2 hours | 52.7 | 22 |
| 21 | 0.20% F108 | No | Yes | 60° C. | 2 hours | 53.9 | 17 |

[a]The amount of BHA and SO$_2$ applied to the cyanoacrylate monomer in each reaction is different.
[b]Highly viscous cyanoacrylate gel is obtained and no measurement of viscosity is available.

According to the present invention, the viscosity level of the cyanoacrylate adhesive compositions can be controlled. The viscosity level of the cyanoacrylate adhesive compositions is determined by many factors such as the amount of pluronic polymer, the amount of stabilizer present in the cyanoacrylate monomer, the mixing temperature and the mixing time before quenching the partial polymerization of the cyanoacrylate. The viscosity level of the cyanoacrylate adhesive compositions is dependent upon the rate of partial polymerization of cyanoacrylate. Therefore, to increase the viscosity of the cyanoacrylalte adhesive one can increase the amount of pluronic polymer, decrease the amounts of the stabilizers, increase the mixing temperature and increase the mixing time Introducing a predetermined amount of pluronic polymer is into the cyanoacrylate monomer (without or with stabilizers) and mixing the pluronic polymer with the cyanoacrylate monomer to homogeneity at mildly elevated temperatures initiates the partial polymerization of cyanoacrylate. The viscosity of the cyanoacrylate adhesive composition increases as the polymerization of the cyanoacrylate monomer proceeds. Compared to the cyanoacrylate monomer in the absence of stabilizers, the partial polymerization rate of the cyanoacrylate monomer pre-stabilized with stabilizer is easier to control, as is the viscosity level of cyanoacrylate adhesive composition. Once the partial polymerization of cyanoacrylate monomer is initiated, polymerization will continue until it is quenched by the addition of stabilizers. In the preferred embodiments of the present invention, the viscosity of the cyanoacrylate adhesive composition may be determined using a viscometer and once a desired level of viscosity is reached stabilizers may be immediately added to quench the polymerization so that the viscosity of said cyanoacrylate compositions can be stabilized at the desired level. The quenching of the partial polymerization may be accomplished by the addition of free radical stabilizer, anionic stabilizer and/or the combination of free radical and anionic stabilizer. In embodiments of the present invention, the free radical stabilizer is, but not limited to butylated hydroxyl anisole (BHA). BHA may be used in an amount of about 200 to about 15000 ppm of cyanoacrylate compositions preferably about 1000 to about 10000 ppm, more preferably about 2000 to about 8000 ppm. The preferred anionic stabilizer is, but not limited to sulfur dioxide in an amount of about 2 to about 500 ppm, preferably about 10 to about 200 ppm.

The amount of pluronic polymer additive that is added to the monomer composition depends upon the desired level of viscosity and cure speed and the concentration of stabilizers present in cyanoacrylate monomers. The pluronic polymer additive present in the adhesive compositions of the present invention is preferably about 0.01-0.80% by weight of the adhesive composition. In preferred embodiments, the pluronic polymer additive is present in an amount of about 0.03% to about 0.50%, and more preferably about 0.05% to about 0.20% of the adhesive composition.

Another advantage of the current invention is to provide a method of improving the cure speed and viscosity with a small amount of polymer additive. In preferred embodiments, less than 0.20% of pluronic polymer by weight is added to the cyanoacrylate adhesive compositions. With the addition of the pluronic polymer the amount of the thickening agent needed to obtain the desired viscosity may be less than those in prior art compositions. The prior art discloses thickener content from about 1% to about 30% by weight of the cyanoacrylate adhesive compositions and generally between from about 3% to 10% by weight. Such a large amount of thickening agent in the adhesive composition results in the reduction of bond strength, curing ability and optical clarity of the cyanoacrylate adhesive.

In order to evaluate the effect of temperature on the performance of cyanoacrylate compositions of the present invention, the cyanoacrylate adhesive compositions have been prepared by adding the pluronic polymer to the cyanoacrylate adhesives at various temperatures. As shown in Table 2, the cyanoacrylate adhesive compositions were subjected to temperatures in the range from about 40 to about 60° C. Below 40 IC, it takes more time to induce the partial polymerization for a desired viscosity. If the temperature is above 60° C., it is difficult to control the partial polymerization once it is initiated. The mixing time shown in Table 2 is the time to stir and heat the cyanoacrylate adhesive in the presence of pluronic polymer before quenching the partial polymerization by stabilizers. The mixing time also affects the performance of the cyanoacrylate compositions. The longer the mixing time, the more viscous the cyanoacrylate adhesives become.

Methods of the present invention provide cyanoacrylate adhesive compositions of desired viscosity with a fast cure speed. As shown in Table 2, cyanoacrylate adhesive compositions with any desired level of viscosity were prepared by modifying the amount of polymer additive and free radical or anionic stabilizers present in the cyanoacrylate monomer and varying the mixing temperature and time.

The present invention also provides stable cyanoacrylate adhesive compositions with a desired level of viscosity. The stability of the cyanoacrylate adhesive compositions may be evaluated by the accelerated aging and viscosity test. The accelerated aging test of cyanoacrylate adhesive composition is performed in the oven at 80° C. for a period of 12 days. The cyanoacrylate compositions are tested for viscosity at intervals of 3, 6, 9 and 12 days. Based on prior stability studies for cyanoacrylate compositions and ASTM method, 12 days accelerated aging at 80° C. correlates to 2 years of shelf life at ambient temperatures (ASTM F1980-2). The accelerated aging test at 80° C. is initially conducted for bulk cyanoacrylate adhesive compositions with the desired level of high viscosity before packaging and sterilizing. Throughout the entire aging procedure, all cyanoacrylate adhesive samples remain fluid consistency. The stability of the cyanoacrylate adhesive samples is confirmed by viscosity test, as shown in Table 3.

TABLE 3

Performance of the cyanoacrylate adhesive compositions with different levels of viscosity before and after the accelerated aging at 80° C.

| Formulations | Average viscosity before and after accelerated aging (cps) | | | | |
| --- | --- | --- | --- | --- | --- |
| | Day 0 | Day 3 | Day 6 | Day 9 | Day 12 |
| 1 | 52.3 | 52.9 | 53.9 | 57.4 | 66.6 |
| 2 | 50.5 | 55.4 | 59.7 | 67.3 | 71.1 |
| 3 | 174.9 | 178.2 | 180.8 | 199.4 | 213 |
| 4 | 17.3 | 17.6 | 19.2 | 24.5 | 25.3 |
| 5 | 155.3 | 152.8 | 162.2 | 174.9 | 185.1 |

It is desirable for the viscosity of the adhesive compositions to remain the same before and after the aging test, however as a practical matter the acceptable viscosity range is the viscosity level at which the adhesive is still dispensable via an applicator and the adhesives perform well. In most cases the viscosity of the test sample increases throughout the aging test. Depending on the starting viscosity (day 0) the viscosity of the composition should not exceed 3000 cp nor decrease to below 10 cp. Preferably the range of viscosity should be between about 20 to about 2000 cp and more preferably between about 30 to about 1000 cp. The change of the viscosity (either increase or decrease) of the cyanoacrylate adhesive compositions from day 0 to day 12 of the accelerated aging test may be about 0% to about 100%, preferably about 0% to about 50% and more preferably from about 0% to about 20%.

Cyanoacrylate adhesive compositions for medical application are preferably sterile. The cyanoacrylate compositons of the present invention can be sterilized by common techniques. Sterilization of the cyanoacryolate adhesive compositions is preferably accomplished by methods including, but not limited to, chemical, physical, and irradiation methods. Examples of chemical methods include, but are not limited to, exposure to ethylene oxide. Examples of irradiation methods include, but are not limited to, gamma irradiation, electron beam irradiation, and microwave irradiation. Preferred methods of sterilization are chemical sterilization and electron beam sterilization.

The viscosity level of the cyanoacrylate adhesive compositions often change after sterilization. Prior art cyanoacrylate adhesives demonstrated 400% increase or more in viscosity induced by sterilization. Often sterilization is used to increase the viscosity of cyanoacrylate adhesives. The compositions and methods of the present invention minimize the variation in viscosity of cyanoacrylate adhesives due to sterilization. Conversely the presence of polymer thickening agents disclosed in the prior art may induce a dramatic decrease of the viscosity of the cyanoacrylate adhesive compositions. This decrease in viscosity may be due to the fact that certain polymer thickening agents are prone to decomposition during sterilization. The cyanoacrylate adhesive compositions of the present invention decrease the variability seen in viscosity of cyanoacrylate adhesives before and after sterilization. The cyanoacrylate adhesive compositions of the present invention include changes in viscosity as measured before and after sterilization of between about 0% and 250%, preferably a change in viscosity between about 0% and about 100% and more preferably between about 0% and about 50%.

According to the preferred embodiments, the cyanoacrylate compositions of the current invention are sterile and the polymer additives are biocompatible, making the cyanoacrylate compositions especially suitable for use in medical applications. In use, the cyanoacrylate adhesive composition is applied to the desired tissue area as a liquid which then polymerizes upon contact with tissue. The desired viscosity of the cyanoacrylate adhesive compositions prevents the runniness of the adhesives encountered by the low viscosity adhesive compositions. The pluronic polymer additives also serve as the cure speed accelerator which allows for quick polymerization and setting of the cyanoacrylate adhesive compositions.

The method of the current invention can be applied to any cyanoacrylate, preferably a 2-cyanoacrylate ester monomer. The 2-cyanoacrylate is preferably an aliphatic cyanoacrylate ester and preferably an alkyl, cycloalkyl, alkenyl and alkoxyalkyl, 2-cyanoacrylate ester. The alkyl group may contain from 2 to 12 carbon atoms, and is preferably a $C_2$ to $C_8$ alkyl ester, and is most preferably a $C_4$ to $C_8$ alkyl ester. Suitable 2-cyanoacrylate esters include without limitation, the ethyl, n-propyl, iso-propyl, n-butyl, pentyl, hexyl, cyclohexyl, heptyl, n-octyl, 2-octyl, 2-ethylhexyl, 2-methoxyethyl and 2-ethoxyethyl esters. The 2-cyanoacrylate monomers may be used alone, or they may be used in mixtures.

The 2-cyanoacrylate monomers of the invention may be synthesized by following the procedures known in the prior art such as U.S. Pat. Nos. 4,364,876, 2,721,858 and 3,254,111, the contents of which, are incorporated by reference. Cyanoacrylates used in the current invention may be prepared by reacting cyanoacetate with formaldehyde in the presence of a basic condensation catalyst at high temperature to give a low molecular weight polymer. A depolymerization step followed under high temperature and high vacuum in the presence of acidic and anionic inhibitors, yielding a crude monomer that can be distilled under high vacuum in the presence of radical and acidic inhibitors. The distilled 2-cyanoacrylate monomers may then be formulated with free radical and acidic inhibitors depending upon their application and stability.

The 2-cyanoacrylate compositions may contain one or more free radical polymerization inhibitors. Examples of such radical inhibitors include but are not limited to, hydroquinone, catechol, hydroquinone monomethyl ether and hindered phenols such as butylated hydroxyanisol, 4-ethoxyphenol, butylated hydroxytoluene (2,6-di-tert-butyl butylphenol and 4-methoxyphenol), 3 methoxyphenol, and 2-tert-butyl-4methoxyphenol; 2,2methylene-bis-(4-methyl-6-tert-butylphenol).

The 2-cyanoacrylate compositions may contain one or more acidic inhibitors in the range from 10 to 6000 ppm. Such acidic inhibitors include but are not limited to: sulfur dioxide, nitrogen oxide, boron oxide, phosphoric acid, ortho, meta, or para-phosphoric acid, acetic acid, tri-fluoroacetic acid, benzoic acid, cyanoacetic acid, tribromoacetic acid, trichloroacetic acid, sulfuric acid, perchloric acid, boron trifluoride, fluorosulfonic acid, sulfonic acid, hydrogen fluoride, hydrochloric acid, hydrobromic acid, chlorosulfonic acid, and toluenesulfonic acid.

Vinyl pyrrolidone polymers and copolymers may be applied to reduce the amount of contaminants and extraneous additives in the cyanoacrylate monomer which can lead to several problems including premature polymerization. These particulate agents are combined with the monomer adhesive in mutual contact until the adhesive is destabilized. In order to achieve the mutual contact, vinyl pyrrolidone polymer is mixed with the cyanoacrylate monomer under vacuum for a minimum of 3 hours, which may remove possible acid residues to destabilize the adhesive. The solid powder of vinyl pyrrolidone polymer is then removed from cyanoacrylate adhesive by filtering through a 0.2 μm filter.

The 2-cyanoacrylate compositions with the desired level of increased viscosity may contain small amounts of dyes such as the derivatives of anthracene and other complex structures. Some of these dyes include but are not limited to, 1-hydroxy-4-[4-methylphenylamino]-9,10 anthracenedione (D&C violet No. 2); 9-(o-carboxyphenyl)-6-hydroxy -2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); and 2-(1,3dihydro-3-oxo-5-sulfo-2H-indole-2-ylidine)-2,3-dihydro -3-oxo-1H-ind-ole-5-sulfonic acid disodium salt (FD&C Blue No. 2).

The following non-limiting examples are intended to further illustrate the current invention.

EXAMPLES

Example 1

93.6 pounds of 2-octyl cyanoacrylate was charged into stainless steel container equipped with the mechanical agitator. 106.2 g of polyclar super R was added to the system, which was mixed under vacuum for a minimum of 3 hours. Then the monomer was filtered using 100 micron filter. BHA, D&C Violet and $SO_2$ were added to the container and stirred for a minimum of 0.5 hour. After the mixing is complete, the monomer was further filtered through a 0.2 micron filter. After the filtration, the resulting cyanoacrylate adhesive composition was subjected to viscosity, set time, bond strength and accelerated aging tests.

Example 2

To a three neck round bottom flask equipped with a thermometer and a magnetic stir bar, 111.5 g of 2-octyl cyanoacrylate composition stabilized with BHA and $SO_2$ was mixed with 245 mg of pluronic F127 and stirred at 60° C. for 2 hours. After it cools down, the highly viscous 2-octyl cyanoacrylate gel was obtained.

Example 3

To a three neck round bottom flask equipped with a thermometer and a magnetic stir bar, 118 g of 2-octyl cyanoacrylate monomer stabilized with BHA and $SO_2$ was mixed with 189 mg of pluronic F127 and stirred at 60° C. for 2 hours. After it cools down, the resulting cyanoacrylate adhesive composition was subjected to viscosity and set time test. The average set time for the sample is 17 s and the average viscosity for the sample is 58.9 cp.

Example 4

To a three neck round bottom flask equipped with a thermometer and a magnetic stir bar, 176.2 g of 2-octyl cyanoacrylate monomer stabilized with BHA and $SO_2$ was mixed with 705 mg of pluronic F68 and stirred at 60° C. for 1.5 hours. After it cools down, the resulting cyanoacrylate adhesive composition was subjected to viscosity and set time test. The average set time for the sample is 12 s and the average viscosity for the sample is 182.5 cp.

Example 5

To a three neck round bottom flask equipped with a thermometer and a magnetic stir bar, 171.8 g of 2-octyl cyanoacrylate monomer stabilized with BHA and $SO_2$ was mixed with 515 mg of pluronic F68 and stirred at 60° C. for 1.5 hours. After it cools down, the resulting cyanoacrylate adhesive composition was subjected to viscosity and set time test. The average set time for the sample is 22 s and the average viscosity for the sample is 51.9 cp.

Example 6

To a three neck round bottom flask equipped with a thermometer and a magnetic stir bar, 111.1 g of 2-octyl cyanoacrylate monomer stabilized with BHA and $SO_2$ was mixed with 444 mg of pluronic F88 and stirred at 60° C. for 2 hours. After it cools down, the resulting cyanoacrylate adhesive composition was subjected to viscosity and set time test. The average set time for the sample is 13 s and the average viscosity for the sample is 23.8 cp.

Example 7

To a three neck round bottom flask equipped with a thermometer and a magnetic stir bar, 154.6 g of 2-octyl cyanoacrylate monomer stabilized with BHA and $SO_2$ was mixed with 696 mg of pluronic F88 and stirred at 60° C. for 2 hours. After it cools down, the resulting cyanoacrylate adhesive composition was subjected to viscosity and set time test. The average set time for the composition is 19 s and the average viscosity for the composition is 107.7 cp.

Example 8

To a three neck round bottom flask equipped with a thermometer and a magnetic stir bar, 144.7 g of 2-octyl cyanoacrylate monomer stabilized with BHA and $SO_2$ was mixed with 289 mg of pluronic F38 and stirred at 60° C. for 1.5 hours. After it cools down, the highly viscous 2-octyl cyanoacrylate gel was obtained.

Example 9

To a three neck round bottom flask equipped with a thermometer and a magnetic stir bar, 167.9 g of 2-octyl cyanoacrylate monomer stabilized with BHA and $SO_2$ was mixed with 269 mg of pluronic F38 and stirred at 60° C. for 1.5 hours. After it cools down, the resulting cyanoacrylate adhesive composition was subjected to viscosity and set time test. The average set time for the sample is 15 s and the average viscosity for the sample is 51.9 cp.

Example 10

To a three neck round bottom flask equipped with a thermometer and a magnetic stir bar, 123.5 g of 2-octyl cyanoacrylate monomer stabilized with a very small amount of BHA and $SO_2$ was mixed with 371mg of pluronic F68 was added and stirred at 60° C. for 100 minutes. After cooling down to room temperature, highly viscous 2-octyl cyanoacrylate gel was obtained, to which BHA, $SO_2$, and D&C Violet were added.

Example 11

To a three neck round bottom flask equipped with a thermometer and a magnetic stir bar, 88.1 g of 2-octyl cyanoacrylate monomer stabilized with a very small amount of BHA and $SO_2$ was mixed with 106 mg of pluronic F127 and stirred at 60° C. for 2.5 hours. After cooling down to room temperature, suitable amount of BHA, $SO_2$ and D&C Violet were added and the resulting cyanoacrylate adhesive composition was subjected to viscosity and set time test. The average set time for the sample is 35 s and the average viscosity for the sample is 142.4 cp.

Example 12

To a three neck round bottom flask equipped with a thermometer and a magnetic stir bar, 107.3 g of 2-octyl cyanoacrylate monomer stabilized with a very small amount of BHA and $SO_2$ was mixed with 193 mg of pluronic F88 and stirred at 60° C. for 2 hours. After cooling down to 55° C., suitable amount of BHA, $SO_2$ and D&C Violet were added to the resulting 2-octyl cyanoacrylate gel.

Example 13

To a three neck round bottom flask equipped with a thermometer and a magnetic stir bar, 114.8 g of 2-octyl cyanoacrylate monomer stabilized with BHA and $SO_2$ was mixed with 628 mg of pluronic F108 NF and stirred at 60° C. for 2 hours. After cooling down to room temperature, highly viscous 2-octyl cyanoacrylate gel was obtained.

Example 14

To a three neck round bottom flask equipped with a thermometer and a magnetic stir bar, 106.4 g of 2-octyl cyanoacrylate monomer stabilized with a very small amount of BHA and $SO_2$ was mixed with 213 mg of pluronic F108 NF and stirred at 60° C. for 50 minutes. After cooling down to 50° C., suitable amount of BHA, $SO_2$ and D&C Violet were added and the resulting cyanoacrylate adhesive composition was subjected to viscosity and set time test. The average set time for the sample is 17 s and the average viscosity for the sample is 53.9 cp.

What is claimed is:

1. A method of preparing a sterile cyanoacrylate adhesive composition with a controlled level of high viscosity and a fast curing speed comprising:
    a. mixing at least one poloxamer with a cyanoacrylate adhesive at a temperature of about 30° C. to about 70° C. for about 1 hour to about 3 hours to dissolve the poloxamer, initiate partial polymerization of the cyanoacrylate adhesive, and increase the viscosity of the adhesive composition to a desired level;
    b. after increasing the viscosity of the adhesive composition to the desired level according to step (a), adding a free radical polymerization inhibitor, an anionic polymerization inhibitor, or a combination thereof to the adhesive composition to quench the partial polymerization of the cyanoacrylate adhesive; and
    c. sterilizing the adhesive composition after quenching the partial polymerization according to step (b) to produce the sterile cyanoacrylate adhesive composition.

2. The method of claim 1, wherein the sterile adhesive composition has a curing time of less than 35 seconds.

3. The method of claim 1, wherein the sterile adhesive composition is a highly viscous gel.

4. The method of claim 1, wherein the at least one poloxamer enhances the viscosity and the curing speed of the sterilized adhesive composition.

5. The method of claim 1, wherein the at least one poloxamer is not soluble in cyanoacrylate without application of heat.

6. The method of claim 1, wherein the amount of poloxamer is from about 0.01% by weight to about 0.80% by weight of the sterilized adhesive composition.

7. The method of claim 1, wherein the cyanoacrylate adhesive is a 2-cyanoacrylate ester selected from the group consisting of alkyl, cycloalkyl or alkylalkoxyl cyanoacrylate ester.

8. The method of claim 1, wherein the at least one poloxamer has the following formula:

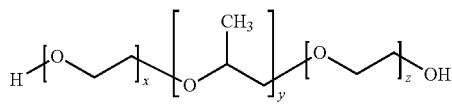

wherein x is from 5 to 200, y is from 5 to 100, and z is from 5 to 200.

9. The method of claim 1, wherein the poloxamer additive is selected from the group consisting of poloxamer 238, poloxamer 188, poloxamer 108, poloxamer 338, poloxamer 407, and mixtures thereof.

10. The method of claim 9, wherein the poloxamer additive is poloxamer 407 in an amount of from about 0.04% to about 0.22% by weight of the sterile adhesive composition.

11. The method of claim 9, wherein the poloxamer additive is poloxamer 238 in an amount of from about 0.16% to about 0.45% by weight of the sterile adhesive composition.

12. The method of claim 9, wherein the poloxamer additive is poloxamer 108 in an amount of from about 0.1% to about 0.2% by weight of the sterile adhesive composition.

13. The method of claim 9, wherein the poloxamer additive is poloxamer 188 in an amount of from about 0.06% to about 0.4% by weight of the sterile adhesive composition.

14. The method of claim 9, wherein the poloxamer additive is poloxamer 338 in an amount of from about 0.1% to about 0.5% by weight of the sterile adhesive composition.

15. The method of claim 1, wherein the mixture is sterilized by irradiation sterilization.

16. The method of claim 1, wherein the mixture is sterilized by chemical sterilization.

17. The method of claim 1, wherein the anionic polymerization inhibitor is selected from the group consisting of: sulfur dioxide, boron oxide, phosphoric acid, acetic acid, benzoic acid, cyanoacetic acid, 1,4-butane sultone, boron trifluoride, perchloric acid, hydrochloric acid, sulfuric acid, sulfonic acid, and mixtures thereof.

18. The method of claim 1, wherein the free radical polymerization inhibitor is selected from the group consisting of: hydroxyanisole, hydroquinone, catechol, hydroquinone monomethyl ester, butylated hydroxytoluene, 4-ethoxyphenol, 4-methoxyphenol, and mixtures thereof.

19. The method of claim 1, wherein the cyanoacrylate adhesive is pre-stabilized with a free radical polymerization inhibitor, an anionic polymerization inhibitor, or a combination thereof.

20. The method of claim 1, wherein the desired level of viscosity is between about 20 cp and about 2000 cp.

* * * * *